United States Patent
Wang et al.

(10) Patent No.: US 10,441,600 B2
(45) Date of Patent: Oct. 15, 2019

(54) OLIGODEOXY NUCLEOTIDE FOR PREPARING DRUGS FOR INHIBITING TUMOR GROWTH AND APPLICATION THEREOF

(71) Applicants: Nanjing New Industry Investment Group Co., Ltd., Nanjing, Jiangsu (CN); Jiangsu Keygen Biotech Corp., Ltd, Nanjing, Jiangsu (CN)

(72) Inventors: Xuegen Wang, Jiangsu (CN); Qing Ye, Jiangsu (CN); Yijun Sun, Jiangsu (CN)

(73) Assignees: JIANGSU KEYGEN BIOTECH CORP., LTD, Nanjing, Jiangsu (CN); NANJING NEW INDUSTRY INVESTMENT GROUP CO., LTD, Nanjing, Jiangsu (CN)

( * ) Notice: Subject to any disclaimer, the term of this patent is extended or adjusted under 35 U.S.C. 154(b) by 44 days.

(21) Appl. No.: 15/538,288

(22) PCT Filed: Jun. 25, 2015

(86) PCT No.: PCT/CN2015/082408
§ 371 (c)(1),
(2) Date: Jun. 21, 2017

(87) PCT Pub. No.: WO2016/107118
PCT Pub. Date: Jul. 7, 2016

(65) Prior Publication Data
US 2018/0140627 A1    May 24, 2018

(30) Foreign Application Priority Data
Dec. 30, 2014 (CN) .......................... 2014 1 0844012

(51) Int. Cl.
*C12N 15/11* (2006.01)
*A61K 31/7125* (2006.01)
*A61K 31/713* (2006.01)
*C12N 15/113* (2010.01)
*A61P 35/00* (2006.01)

(52) U.S. Cl.
CPC ........ *A61K 31/7125* (2013.01); *A61K 31/713* (2013.01); *A61P 35/00* (2018.01); *C12N 15/113* (2013.01); *C12N 2310/11* (2013.01); *C12N 2310/14* (2013.01); *C12N 2310/315* (2013.01); *C12N 2330/30* (2013.01); *C12Q 2600/106* (2013.01); *C12Q 2600/136* (2013.01)

(58) Field of Classification Search
None
See application file for complete search history.

(56) References Cited

U.S. PATENT DOCUMENTS

2011/0250261 A1* 10/2011 Lee ...................... C12N 15/113
424/450

FOREIGN PATENT DOCUMENTS

| CN | 1507873 | 6/2004 | |
|---|---|---|---|
| CN | 1507874 | 6/2004 | |
| CN | 1507875 | 6/2004 | |
| WO | WO-0121644 A2 * | 3/2001 | ........... C07K 14/415 |

OTHER PUBLICATIONS

International Search Report and Written Opinion of PCT/CN2015/082403 dated Sep. 29, 2015, 12 pages (English and Chinese).
Wang, Xuegen, et al. "Antitumor activity of decoy oligonucleotides targeted to AP-1 in vitro and in vivo." Progress in Biochemistry and Biophysics, vol. 31, No. 1, Dec. 31, 2004, ISSN: pp. 27-31 (Abstract only).

* cited by examiner

*Primary Examiner* — Ekaterina Poliakova-Georgantas
(74) *Attorney, Agent, or Firm* — Rankin, Hill & Clark LLP

(57) ABSTRACT

The present invention provides an oligodeoxy nucleotide for preparing drugs for inhibiting tumor growth and an application thereof. The core sequences of the oligodeoxy nucleotide is TTTCSCGCS, wherein S is C or G. The oligodeoxy nucleotide above further comprises an antisense strand and a modified type thereof. The oligodeoxy nucleotide according to the present invention plays a role of inhibiting the tumor growth in vitro and vivo, and is expected to be used for preparing drugs for inhibiting tumor growth, with high specificity and high inhibition ratio.

17 Claims, 3 Drawing Sheets
Specification includes a Sequence Listing.

Inhibiting effect of K17 to growth of human breast cancer cell MDA-MB-231 xenograft tumor in nude mice

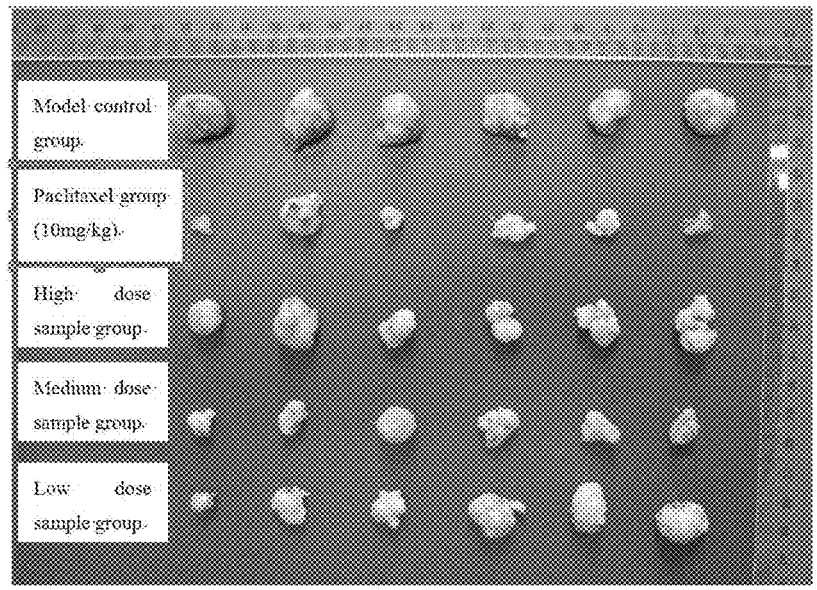
Fig. 3 Inhibiting effect of KT17 to growth of human breast cancer cell MDA-MB-231 xenograft tumor in nude mice
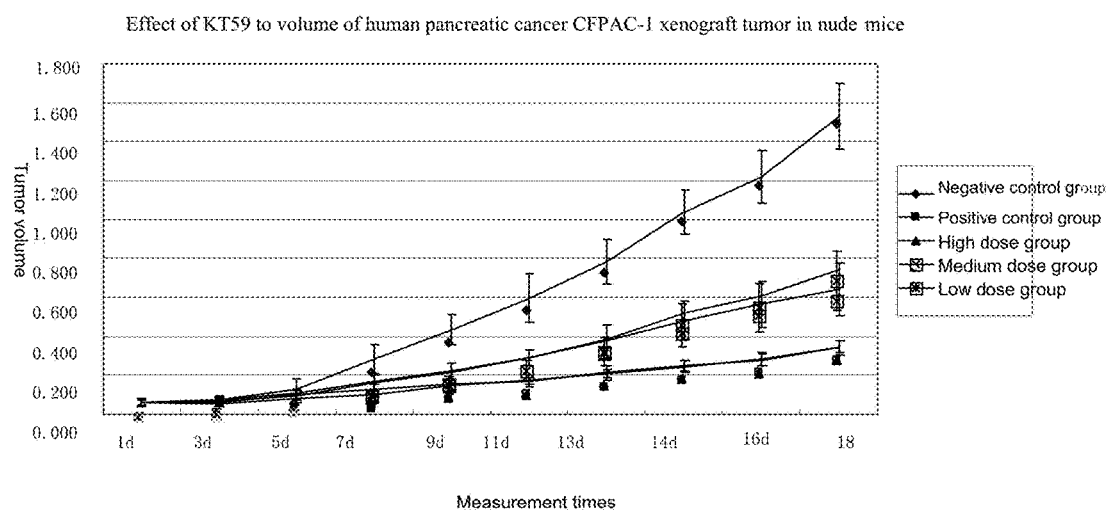
Fig. 4

OLIGODEOXY NUCLEOTIDE FOR PREPARING DRUGS FOR INHIBITING TUMOR GROWTH AND APPLICATION THEREOF

TECHNICAL FIELD

The present invention belongs to the biological medicine field, and specifically relates to an oligodeoxy nucleotide for preparing drugs for inhibiting tumor growth and an application thereof.

BACKGROUND

An oligodeoxy nucleotide may include an antisense nucleic acid, a small interfering RNA, an aptamer, a micro-RNA, a DECOY nucleic acid, or the like, which respectively play biological functions thereof according to different effect target spots and mechanisms. The oligodeoxy nucleotide used as a therapeutic drug has been listed in USA. Meanwhile, dozens of drugs are under clinical research. With the progress of biotechnology, drug screening and preparation and other technologies, more and more oligodeoxy nucleotides with specific functions are discovered, and are developed and applied for treating, preventing and diagnosing various diseases.

BRIEF DESCRIPTION

Object of the Invention the present invention is intended to provide an oligodeoxy nucleotide for preparing drugs for inhibiting tumor growth and an application thereof. Through screening series oligodeoxy nucleotides Oligo dsDNA, and testing the cancer inhibition activity the oligodeoxy nucleotides of the sequences 1-10 have an inhibiting effect on the tumor growth in vitro and vivo.

Technical solution

In order to achieve the technical object above, the present invention provides an oligodeoxy nucleotide for preparing drugs for inhibiting tumor growth, wherein the oligodeoxy nucleotide is any one of the following sequences 1-10:

```
sequence 1:
                                        (SEQ ID NO: 1)
5'-CTTGAGGGGAATTTCCCAG-3' sequence 2:
                                        (SEQ ID NO: 2)
5'-GAGAGGGGACTTTCCGAGAG-3' sequence 3:
                                        (SEQ ID NO: 3)
5'-CCTTGAAGGGATTTCCCTCC-3'

Sequence 4:
                                        (SEQ ID NO: 4)
5'-GCCATTTCCGGGAATTGCTA-3' sequence 5:
                                        (SEQ ID NO: 5)
5'-AGTTCTGGGAATTCC-3' sequence 6:
                                        (SEQ ID NO: 6)
5'-AGTCATTTCCGGGAAATGACT-3' sequence 7:
                                        (SEQ ID NO: 7)
5'-TGACTATTTCCCGCGACTT-3' sequence 8:
                                        (SEQ ID NO: 8)
5'-TTGACTATTTCCCGCCACTT-3' sequence 9:
                                        (SEQ ID NO: 9)
5'-ATCTATTTCGCGCCCTTATG-3'
and sequence 10:
                                        (SEQ ID NO: 10)
5'  TTAAGTTTCGCGCCCTTTCTC-3'.
```

The oligodeoxy nucleotide may also an antisense strand of the sequences 1-10 above.

As another embodiment, the oligodeoxy nucleotide is a modified type of the oligodeoxy nucleotide above.

To be specific, the modified type is special locus phosphorothioate modification; or phosphorothioate modification with three nucleotides at two ends; or full phosphorothioate modification.

Preferably, the modified locus corresponding to each sequence is as follows:

```
positions 1, 2, 5, 6, 16 and/or 17 of sequence 1
(positive):
                                        (SEQ ID NO: 1)
5'-CTTGAGGGGAATTTCCCAG-3' positions 1, 2, 5, 6, 14 and/or 15 of sequence 2
(positive):
                                        (SEQ ID NO: 2)
5'-GAGAGGGGACTTTCCGAGAG-3' positions 1, 2, 5, 6, 16 and/or 17 of sequence 3
(positive):
                                        (SEQ ID NO: 3)
5'-CCTTGAAGGGATTTCCCTCC-3' positions 1, 2, 4, 5, 15 and/or 16 of sequence 4
(positive):
                                        (SEQ ID NO: 4)
5'-GCCATTTCCGGGAATTGCTA-3' positions 1, 2, 3, 13, 14 and/or 15 of sequence 5
(positive):
                                        (SEQ ID NO: 5)
5'-AGTTCTGGGAATTCC-3' positions 1, 2, 5, 6, 16 and/or 17 of sequence 6
(positive):
                                        (SEQ ID NO: 6)
5'-AGTCATTTCCGGGAAATGACT-3' positions 1, 2, 5, 6, 14 and/or 15 of sequence 7
(positive):
                                        (SEQ ID NO: 7)
5'-TGACTATTTCCCGCGACTT-3' positions 1, 2, 5, 6, 15 and/or 16 of sequence 8
(positive):
                                        (SEQ ID NO: 8)
5'-TTGACTATTTCCCGCCACTT-3' positions 1, 2, 5, 6, 15 and/or 16 of sequence 9
(positive):
                                        (SEQ ID NO: 9)
5'-ATCTATTTCGCGCCCTTATG-3'
and positions 1, 2, 5, 6, 15 and/or 16 of sequence 10
(positive):
                                        (SEQ ID NO: 10)
5'-TTAAGTTTCGCGCCCTTTCTC-3'
```

Wherein, the positive means that the positive-sense strand is listed only, and the antisense strand is omitted.

The present invention proposes an application of the oligodeoxy nucleotide used for preparing the drug for inhibiting tumor growth at the same time.

To be specific, the following steps are comprised: purifying the oligodeoxy nucleotide through HPLC, and preparing the oligodeoxy nucleotide into concentration of 1-2 mg/mL by sterilization water, then conducting equal molar ratio mixture to the oligodeoxy nucleotide with an antisense strand thereof, heating the mixture to 80-85° C. for 10-15 min through water bath, cooling the mixture to indoor temperature naturally, and annealing to combine the mixture into double strands for preparing drugs for inhibiting tumor growth.

Wherein, the tumor is any one of lung cancer, breast cancer and pancreatic cancer.

Beneficial effects: the oligodeoxy nucleotide provided by the present invention plays a role of inhibiting the tumor growth in vitro and vivo, and is expected to be used for preparing drugs for inhibiting tumor growth, with high specificity and high inhibition ratio.

BRIEF DESCRIPTION OF THE DRAWINGS

FIG. 3 is a photo of the sequence 5 (KT17) to the growth volume change of the human breast cancer cell MDA-MB-231 xenograft tumor in nude mice;

FIG. 4 is a schematic diagram of a sequence 8 (KT17) to growth volume change of a human pancreatic cancer cell CFPAC-1 xenograft tumor in nude mice.

DETAILED DESCRIPTION

Figure 1:
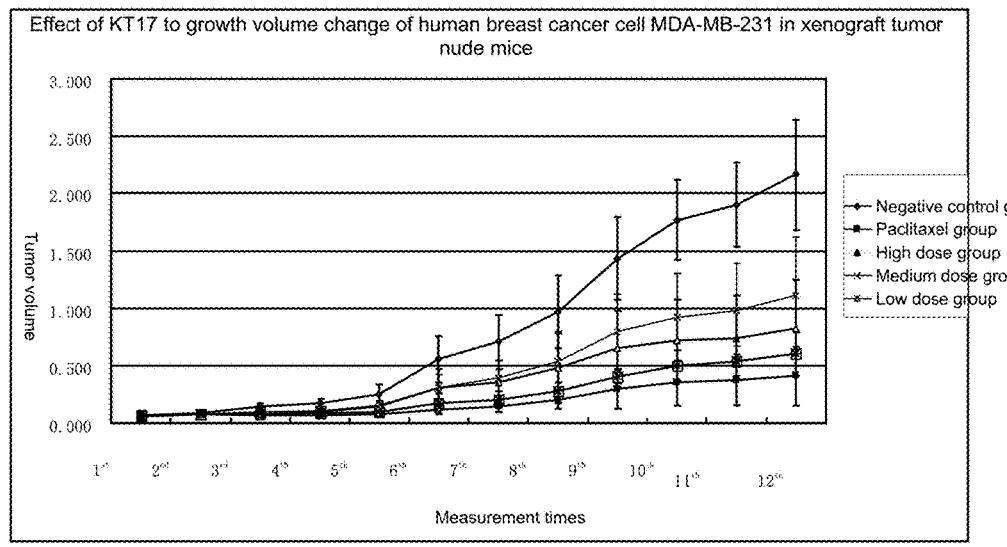
FIG. 1 is a schematic diagram of a sequence 5 (KT17) to growth volume change of human breast cancer cell MDA-MB-231 xenograft tumor in nude mice.

The oligodeoxy nucleotide provided by the present invention mainly includes three types which include 10 sequences in total, and are specifically as follows:

First type: Oligo dsDNA mainly composed of a core sequence RGGGAHTTYCS comprises:

```
sequence 1 (positive):
                                    (SEQ ID NO: 1)
5'-CTTGAGGGGAATTTCCCAG-3' sequence 2 (positive):
                                    (SEQ ID NO: 2)
5'-GAGAGGGGACTTTCCGAGAG-3'
and sequence 3 (positive):
                                    (SEQ ID NO: 3)
5'-CCTTGAAGGGATTTCCCTCC-3'
```

Second type: Oligo dsDNA mainly composed of a core sequence TTYSGGAAWT comprises:

```
sequence 4 (positive):
                                    (SEQ ID NO: 4)
5'-GCCATTTCCGGGAATTGCTA-3' sequence 5 (positive):
                                    (SEQ ID NO: 5)
5'-AGTTCTGGGAATTCC-3'
and sequence 6 (positive):
                                    (SEQ ID NO: 6)
5'-AGTCATTTCCGGGAAATGACT-3'
```

Third type: Oligo dsDNA mainly composed of a core sequence TTTCSCGCS comprises:

```
sequence 7 (positive):
                                    (SEQ ID NO: 7)
5'-TGACTATTTCCCGCGACTT-3' sequence 8 (positive):
                                    (SEQ ID NO: 8)
5'-TTGACTATTTCCCGCCACTT-3' sequence 9 (positive):
                                    (SEQ ID NO: 9)
5'-ATCTATTTCGCGCCCTTATG-3'
and sequence 10 (positive):
                                    (SEQ ID NO: 10)
5'-TTAAGTTTCGCGCCCTTTCTC-3'.
```

Wherein, the positive means that the positive-sense strand is listed only, and the antisense strand is omitted; in the modified types, the first type is part locus phosphorothioate modification, and positions 1, 2, 5, 6, 16 and/or 17 of SEQ ID NO: 1, positions 1, 2, 5, 6, 14 and/or 15 of SEQ ID NO: 2, positions 1, 2, 5, 6, 16 and/or 17 of SEQ ID NO: 3, positions 1, 2, 4, 5, 15 and/or 16 of SEQ ID NO: 4, positions 1, 2, 3, 13, 14 and/or 15 of SEQ ID NO: 5, positions 1, 2, 5, 6, 16 and/or 17 of SEQ ID NO: 6, positions 1, 2, 5, 6, 14 and/or 15 of SEQ ID NO: 7, positions 1, 2, 5, 6, 15 and/or 16 of SEQ ID NO: 8, positions 1, 2, 5, 6, 15 and/or 16 of SEQ ID NO: 9and/or positions 1, 2, 5, 6, 15 and/or 16 of SEQ ID NO: 10 is/are a modified locus/loci, while the other type is phosphorothioate modification; or phosphorothioate modification with three nucleotides at two ends; or full phosphorothioate modification, R=G/A; H=A/C/T; Y=C/T; S=C/G; and W=A/T.

The inhibiting effect of the oligodeoxy nucleotide above to tumors is illustrated hereinafter through specific embodiments.

Embodiment 1 Inhibiting effect of oligodeoxy nucleotide to tumor growth in vitro.

The oligodeoxy nucleotides of the combined sequences 1 to sequence and the and the antisense strands thereof were subjected to three types of different structure modifications at the same time, which were three groups including special locus phosphorothioate (as mentioned above), three base phosphorothioates at two ends, and full phosphorothioate. After the oligodeoxy nucleotides were purified through to purity more than 90%, and prepared to concentration of 1 mg/mL by sterilization water; then equal molar ratio mixture was conducted to the positive-sense and antisense strands, and the mixture was heated to 80-85° C. for 10-15 min through water bath, cooled to indoor temperature naturally, and annealed to combine the mixture into double strands for standby application.

Breast cancer cell strains MDA-MB-231, lung cancer cell strains NCI-H1975, and pancreatic cancer cell strains CFPAC-1 were cultivated respectively in vitro according to a conventional method. When the cells were grown to $10^5$-$10^6$/mL the cells were dissociated and collected, counted and prepared into a cell suspension with concentration of $3$-$5\times10^4$/mL, and 100 μL cell suspension was added into each hole in a 96-hole cell culture plate ($3$-$5\times10^3$ cells for each hole). The 96-hole cell culture plate was put into a 5% $CO_2$ incubator under 37° C. for 24 h; each group of the oligodeoxy nucleotides was diluted to the concentration needed by complete medium, 100 μL corresponding medium containing the oligodeoxy nucleotide was added in each hole, and a negative control group and a positive control group were set at the same time, wherein the negative control group was normal saline, the positive control group is paclitaxel, and a transfection method was subject to a product specification of Lipofectimine; the 96-hole cell culture plate was put into a 5% $CO_2$ under 37° C. for 72 h; 20 μL MTT (5 mg/mL) was added in each hole to cultivate for 4 h in the incubator; the culture medium was discarded, 150 μL DMSO was added in each hole for dissolution, and was evenly and slightly mixed for 10 min through shaking; then an OD value of each hole was read by a microplate reader ($\lambda$=490 nm) to calculate the inhibition ratio.

Method for calculating inhibition ratio of each group:

Inhibition ratio of experimental group=(OD value of negative control group−OD value of experimental group/OD value of positive control group)× 100%

The result of screening in vitro showed that all the three types of modification groups of the sequences 1-10 had a certain inhibiting effect to the tumor cell growth, wherein the special locus phosphorothioate modification group of the sequences 1-10 (see the underlined parts in the sequence table for the phosphorothioate locus) had a better growth inhibiting effect to different tumor cells in vitro. The test result was as shown in Table 1:

TABLE 1

Half inhibition ratio $IC_{50}$ Unit: μM

| Sample | Lung cancer cell strain NCI-H1975 | mammary cancer cell strain MDA-MB-231 | pancreatic cancer cell strain CFPAC-1 |
| --- | --- | --- | --- |
| Sequence 1 | 3.663 | 1.492 | 7.982 |
| Sequence 2 | 3.183 | 2.663 | 2.965 |
| Sequence 3 | 4.062 | 5.831 | 3.225 |
| Sequence 4 | 1.673 | 2.573 | 1.672 |
| Sequence 5 | 1.038 | 0.084 | 0.298 |
| Sequence 6 | 1.329 | 1.588 | 1.661 |
| Sequence 7 | 1.699 | 3.438 | 2.306 |
| Sequence 8 | 0.456 | 0.184 | 1.278 |
| Sequence 9 | 5.497 | 3.024 | 1.137 |
| Sequence 10 | 4.219 | 3.31 | 1.442 |

The experimental results of partial secondary screening were as shown in Table 2 and Table 3:

TABLE 2

Mammary cancer cell strain MDA-MB-231 72 h

| Group | | Inhibition ratio |
| --- | --- | --- |
| Negative control | | 0 |
| positive control | | 87.41% |
| Sequence 5 | 200 nM | 82.55% |
| IC50 = 77.342 nM | 100 nM | 54.58% |
| | 50 nM | 31.35% |
| | 25 nM | 17.29% |
| | 12.5 nM | 13.57% |

TABLE 2-continued

Mammary cancer cell strain MDA-MB-231 72 h

| Group | | Inhibition ratio |
| --- | --- | --- |
| | 6.25 nM | 6.99% |
| | 3.125 nM | 7.90% |
| | 1.5625 nM | 1.91% |

TABLE 3

Pancreatic cancer cell strain CFPAC-1 72 H

| Group | | Inhibition ratio |
| --- | --- | --- |
| Negative control | | |
| positive control | | 88.41% |
| Sequence 8 | 200 nM | 62.73% |
| IC50 = 94.577 nM | 100 nM | 56.55% |
| | 50 nM | 41.86% |
| | 25 nM | 15.47% |
| | 12.5 nM | 1.59% |
| | 6.25 nM | 0.13% |
| | 3.125 nM | −0.83% |
| | 1.5625 nM | −1.64% |

Embodiment 2: inhibiting effect of oligodeoxy nucleotide to growth of human deviated xenograft tumor in animal body.

The nucleic acid samples of the sequence 1, the sequence 5 and the sequence 8 (special locus modification groups) were respectively prepared into cationic liposome preparation, and five groups of control drugs including a paclitaxel control group (positive control group) and a normal saline control group (negative control group), a low dose group, a medium dose group and a high dose group were selected. Tested animals were female BALB/c nude mice (12-15 g, 4-5 weeks), etc. The cultivated tumor cell suspension was collected and inoculated under skins at the right sides of axillae of the nude mice, then the animals were grouped randomly when the tumor grown to 50-75 $mm^3$, and each group had eight animals. Meanwhile, each group of the nude mice was dosed for once each day for 14-18 days. A dosing method was tail vein injection, and the antineoplastic effects of the tested samples were dynamically observed by a method of measuring tumor diameters. The nude mice were put to death after being dosed for 14-18 days, and tumor blocks were taken by operation for weighting and photographing.

A formula of calculating the tumor volume (TV) was as follows:

$$TV = 1/2 \times a \times b^2$$

Wherein, a and b respectively represented length and width.

The relative tumor volume (RTV) was calculated according to the measurement results, and the calculation formula was as follows:

$$RTV = Vt/V0,$$

Wherein V0 was the tumor volume measured when dosing by cage (i.e., d0), and Vt was the tumor volume during each measurement.

The evaluation index of the antineoplastic activity: relative tumor increase rate T/C (%), and the calculation formula was as follows:

$$T/C\ (\%) = \frac{T_{RTV}}{C_{RTV}} \times 100$$

$T_{RTV}$: treatment group RTV; and $C_{RTV}$: model group RTV

The average value was represented by X±SD, the statistical treatment was conducted to the analysis between groups by t inspection, and SPSS (Staffstical Package for the Social Science) 17.0 was applied to conduct statistical analysis to the results.

Figure 2:
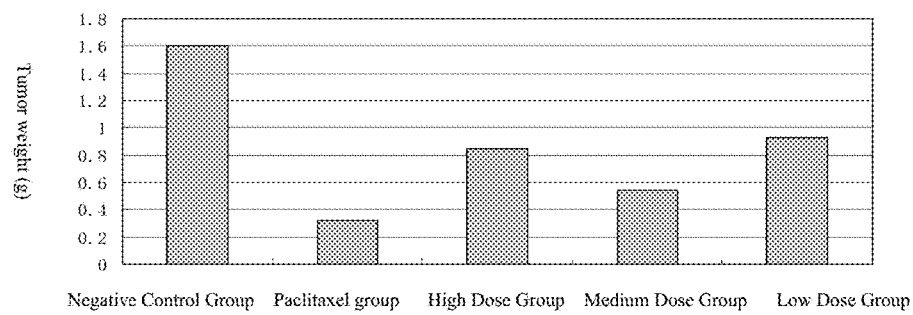
FIG. 2 is a schematic diagram of an inhibiting effect of the sequence 5 (KT17) to the growth of human breast cancer cell MDA-MB-231 xenograft tumor in nude mice.
Figure 5:
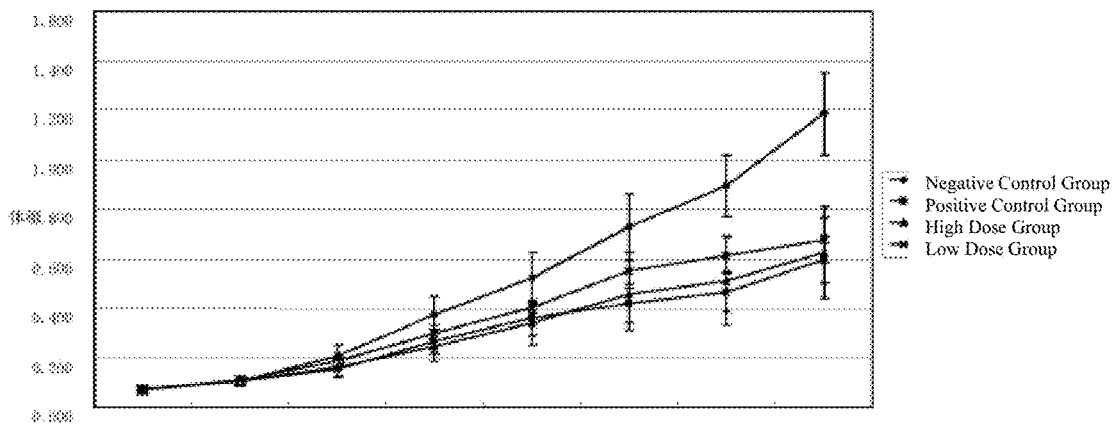
FIG. 5 is a schematic diagram of an inhibiting effect of a sequence 1 (KT17) to the growth of a human lung cancer cell NCI-H1975 xenograft tumor in nude mice.

The results of the pharmacodynamic experiment in vivo above showed that the inhibition ratios of a nucleic acid sequence 5 (KT17) to the high, medium and low dose groups of the breast cancer cells in vivo respectively reached to: 47.13%, 66.42% and 41.81%. As shown in FIGS. 1-3, the inhibition ratios of a nucleic acid sequence 8 (KT59) to the high, medium and low dose groups of the breast cancer cell in vivo respectively reached to: 64.36%, 57.89% and 44.15%; the tumor inhibition ratio was relatively high and there was a certain dose-effect relationship. As shown in FIG. 4, the inhibition ratios of a nucleic acid sequence 1 (KT32) to the high and low dose groups of the breast cancer cell in vivo respectively reached to: 56.35% and 49.44% (as shown in FIG. 5).

In conclusion, the sequences provided by the present invention have obvious inhibiting effect on the tumor growth, and may be selected as candidate drugs for further development.

---

The invention claimed is:

1. An oligodeoxy nucleotide for preparing drugs for inhibiting tumor growth, wherein the oligodeoxy nucleotide is any one of the following sequences:

5'-TGACTATTTCCCGCGACTT-3'; (SEQ ID NO: 7)

5'-TTGACTATTTCCCGCCACTT-3'; (SEQ ID NO: 8)
and

5'-ATCTATTTCGCGCCCTTATG-3'. (SEQ ID NO: 9)

2. An oligodeoxy nucleotide fully complementary to any of the oligodeoxy nucleotides of claim 1.

3. The oligodeoxy nucleotide according to claim 1, wherein the oligodeoxy nucleotide is modified.

4. The oligodeoxy nucleotide according to claim 3, wherein the modification is a phosphorothioate modification; or phosphorothioate modifications of three nucleotides at each end; or full phosphorothioate modification.

5. A method for preparing drugs for inhibiting tumor growth, comprising:

applying the oligodeoxy nucleotide according to claim 1 in preparing drugs for inhibiting tumor growth; and purifying the oligodeoxy nucleotide through HPLC, and preparing the oligodeoxy nucleotide into concentration of 1-2 mg/mL by sterilization water, then conducting equal molar ratio mixture to the oligodeoxy nucleotide with an antisense strand thereof, heating the mixture to 80-85° C. for 10-15 min through water bath, cooling the mixture to indoor temperature naturally, and annealing to combine the mixture into double strands for preparing drugs for inhibiting tumor growth.

6. The oligodeoxy nucleotide according to claim 2, wherein the oligodeoxy nucleotide is modified.

7. The oligodeoxy nucleotide according to claim 6, wherein the modification is a phosphorothioate modification; or phosphorothioate modifications of three nucleotides at each end; or full phosphorothioate modification.

8. A method for preparing drugs for inhibiting tumor growth, comprising:
  applying the oligodeoxy nucleotide according to claim 2 in preparing drugs for inhibiting tumor growth; and
  purifying the oligodeoxy nucleotide through HPLC, and preparing the oligodeoxy nucleotide into concentration of 1-2 mg/mL by sterilization water, then conducting equal molar ratio mixture to the oligodeoxy nucleotide with an antisense strand thereof, heating the mixture to 80-85° C. for 10-15min through water bath, cooling the mixture to indoor temperature naturally, and annealing to combine the mixture into double strands for preparing drugs for inhibiting tumor growth.

9. A method for preparing drugs for inhibiting tumor growth, comprising:
  applying the oligodeoxy nucleotide according to claim 3 in preparing drugs for inhibiting tumor growth; and
  purifying the oligodeoxy nucleotide through HPLC, and preparing the oligodeoxy nucleotide into concentration of 1-2mg/mL by sterilization water, then conducting equal molar ratio mixture to the oligodeoxy nucleotide with an antisense strand thereof, heating the mixture to 80-85° C. for 10-15 min through water bath, cooling the mixture to indoor temperature naturally, and annealing to combine the mixture into double strands for preparing drugs for inhibiting tumor growth.

10. A method for preparing drugs for inhibiting tumor growth, comprising:
  applying the oligodeoxy nucleotide according to claim 4 in preparing drugs for inhibiting tumor growth; and
  purifying the oligodeoxy nucleotide through HPLC, and preparing the oligodeoxy nucleotide into concentration of 1-2 mg/mL by sterilization water, then conducting equal molar ratio mixture to the oligodeoxy nucleotide with an antisense strand thereof, heating the mixture to 80-85° C. for 10-15 min through water bath, cooling the mixture to indoor temperature naturally, and annealing to combine the mixture into double strands for preparing drugs for inhibiting tumor growth.

11. An oligodeoxy nucleotide for preparing drugs for inhibiting tumor growth, wherein a sequence of the oligodeoxy nucleotide consists of the following sequence:

(SEQ ID NO: 10)
5'-TTAAGTTTCGCGCCCTTTCTC-3'.

12. An oligodeoxy nucleotide fully complementary to the oligodeoxy nucleotide of claim 11.

13. The oligodeoxy nucleotide according to claim 11, wherein the oligodeoxy nucleotide is modified.

14. The oligodeoxy nucleotide according to claim 13, wherein the modification is a phosphorothioate modification; or phosphorothioate modifications of three nucleotides at each end; or full phosphorothioate modification.

15. The oligodeoxy nucleotide according to claim 12, wherein the oligodeoxy nucleotide is modified.

16. The oligodeoxy nucleotide according to claim 15, wherein the modification is a phosphorothioate modification; or phosphorothioate modifications of three nucleotides at each end; or full phosphorothioate modification.

17. A method for preparing drugs for inhibiting tumor growth, comprising:
  applying the oligodeoxy nucleotide according to claim 11 in preparing drugs for inhibiting tumor growth; and
  purifying the oligodeoxy nucleotide through HPLC, and preparing the oligodeoxy nucleotide into concentration of 1-2 mg/mL by sterilization water, then conducting equal molar ratio mixture to the oligodeoxy nucleotide with an antisense strand thereof, heating the mixture to 80-85° C. for 10-15 min through water bath, cooling the mixture to indoor temperature naturally, and annealing to combine the mixture into double strands for preparing drugs for inhibiting tumor growth.

\* \* \* \* \*

SEQUENCE LISTING

<160> NUMBER OF SEQ ID NOS: 10

<210> SEQ ID NO 1
<211> LENGTH: 19
<212> TYPE: DNA
<213> ORGANISM: Artificial
<220> FEATURE:
<223> OTHER INFORMATION: Synthesized

<400> SEQUENCE: 1
cttgagggga atttcccag                                                19

<210> SEQ ID NO 2
<211> LENGTH: 20
<212> TYPE: DNA
<213> ORGANISM: Artificial
<220> FEATURE:
<223> OTHER INFORMATION: Synthesized

<400> SEQUENCE: 2
gagaggggac tttccgagag                                               20

<210> SEQ ID NO 3
<211> LENGTH: 20
<212> TYPE: DNA
<213> ORGANISM: Artificial
<220> FEATURE:
<223> OTHER INFORMATION: Synthesized

<400> SEQUENCE: 3
ccttgaaggg atttccctcc                                               20

<210> SEQ ID NO 4
<211> LENGTH: 20
<212> TYPE: DNA
<213> ORGANISM: Artificial
<220> FEATURE:
<223> OTHER INFORMATION: Synthesized

<400> SEQUENCE: 4
gccatttccg ggaattgcta                                               20

<210> SEQ ID NO 5
<211> LENGTH: 15
<212> TYPE: DNA
<213> ORGANISM: Artificial
<220> FEATURE:
<223> OTHER INFORMATION: Synthesized

<400> SEQUENCE: 5

-continued

```
agttctggga attcc                                                    15

<210> SEQ ID NO 6
<211> LENGTH: 21
<212> TYPE: DNA
<213> ORGANISM: Artificial
<220> FEATURE:
<223> OTHER INFORMATION: Synthesized

<400> SEQUENCE: 6
agtcatttcc gggaaatgac t                                             21

<210> SEQ ID NO 7
<211> LENGTH: 19
<212> TYPE: DNA
<213> ORGANISM: Artificial
<220> FEATURE:
<223> OTHER INFORMATION: Synthesized

<400> SEQUENCE: 7
tgactatttc ccgcgactt                                                19

<210> SEQ ID NO 8
<211> LENGTH: 20
<212> TYPE: DNA
<213> ORGANISM: Artificial
<220> FEATURE:
<223> OTHER INFORMATION: Synthesized

<400> SEQUENCE: 8
ttgactattt cccgccactt                                               20

<210> SEQ ID NO 9
<211> LENGTH: 20
<212> TYPE: DNA
<213> ORGANISM: Artificial
<220> FEATURE:
<223> OTHER INFORMATION: Synthesized

<400> SEQUENCE: 9
atctatttcg cgcccttatg                                               20

<210> SEQ ID NO 10
<211> LENGTH: 21
<212> TYPE: DNA
<213> ORGANISM: Artificial
<220> FEATURE:
<223> OTHER INFORMATION: Synthesized

<400> SEQUENCE: 10
ttaagtttcg cgccctttct c                                             21
```